United States Patent [19]

Ueno et al.

[11] Patent Number: 4,666,919

[45] Date of Patent: May 19, 1987

[54] STABILIZED PHARMACEUTICAL COMPOSITION CONTAINING AN ISOCARBOSTYRIL DERIVATIVE

[75] Inventors: Masao Ueno, Tokorozawa; Hironori Kubota, Ueda, both of Japan

[73] Assignees: Nisshin Flour Milling Co., Ltd.; Nisshin Chemicals Co., Ltd., both of Japan

[21] Appl. No.: 758,820

[22] Filed: Jul. 25, 1985

[51] Int. Cl.$^4$ ............................................. A61K 31/47
[52] U.S. Cl. .................................... 514/309; 514/970
[58] Field of Search ............................... 514/309, 970

[56] References Cited

U.S. PATENT DOCUMENTS 4,129,565 12/1978 Fukushima et al. ................ 544/142
4,526,893 7/1985 Takahashi et al. ................. 514/309

FOREIGN PATENT DOCUMENTS 2101990 1/1983 United Kingdom ................ 514/309

OTHER PUBLICATIONS

Chem. Abst. 100: 161785h, (1984), Meijiseika Kaisha.

*Primary Examiner*—Douglas W. Robinson
*Attorney, Agent, or Firm*—Larson and Taylor

[57] ABSTRACT

A stabilized pharmaceutical composition containing 4-(3-tert.-butylamino-2-hydroxy)propoxy-2-methylisocarbostyril or an acid addition salt thereof as the active ingredient is now provided, in which the active ingredient compound is stabilized by addition of at least one of stabilizing agents selected from magnesium silicate, magnesium oxide, hydrotalcite and sodium hydrogen carbonate.

8 Claims, No Drawings

STABILIZED PHARMACEUTICAL COMPOSITION CONTAINING AN ISOCARBOSTYRIL DERIVATIVE

SUMMARY OF THE INVENTION

This invention relates to a stabilized pharmaceutical composition containing 4-(3-tert.-butylamino-2-hydroxy)propoxy-2-methylisocarbostyril or its acid addition salt, particularly its hydrochloride, as the active ingredient and at least one of stabilizig agents for the active ingredient compound. This invention also relates to a method for stabilizing 4-(3-tert.-butylamino-2-hydroxy)propoxy-2-methylisocarbostyril or its acid addition salt by mixing therewith at least one of the stabilizing agents.

BACKGROUND OF THE INVENTION

It is known that an isocarbostyril derivative, 4-(3-tert.-butylamino-2-hydroxy)propoxy-2-methylisocarbostyril or an acid addition salts thereof such as the hydrochloride is especially useful for the therapeutic treatment of heart diseases (see: Japanese Patent Publication (KOKOKU) No. 41673/1978, U.K. Pat. No. 1501149 and U.S. Pat. No. 4,129,565). However, such a pharmaceutical composition containing 4-(3-tert.-butylamino-2-hydroxy)propoxy-2-methylisocarbostyril or an acid addition salt thereof as the active ingredient, in association with a pharmaceutically acceptable solid carrier for the active ingredient can always exhibit such disadvantages that the effective content of the isocarbostyril compound as the active ingredient is decreased or reduced during storage of the pharmaceutical composition with lapse of time, and that the whole composition is discolored into brown in appearance.

We, the present inventors, have made extensive researches in an attempt to eliminate the above-mentioned disadvantages usually observed with the pharmaceutical compositions comprising as the active ingredient the 4-(3-tert.-butylamino-2-hydroxy)propoxy-2-methylisocarbostyril or a pharmaceutically acceptable acid addition salt thereof together with the solid carrier for the active ingredient, and as a result we have now found that the isocarbostyril compound used as the active ingredient can be stabilized by adding thereto and mixing with an amount of one or more of such stabilizing agents which are chosen from magnesium silicate, magnesium oxide, hydrotalcite [$Mg_6Al_2(OH)_{16}CO_3 4H_2O$] and sodium hydrogen carbonate. We have thus accomplished this invention.

DETAILED DESCRIPTION OF THE INVENTION

According to a first aspect of this invention, therefore, there is provided a stabilized pharmaceutical composition, which comprises 4-(3-tert.-butylamino-2-hydroxy)propoxy-2-methylisocarbostyril or a pharmaceutically acceptable acid addition salt thereof as the active ingredient, and an amount of at least one of the stabilizing agents selected from magnesium silicate, magnesium oxide, hydrotalcite and sodium hydrogen carbonate.

The stabilized pharmaceutical composition of this invention may further contain a known pharmaceutically acceptable solid carrier or vehicle which is associated with the active ingredient compound and the stabilizing agent(s) used. In this composition, the active isocarbostyril compound may be in the form of the pharmaceutically acceptable acid addition salt such as hydrochloride, sulfate, phosphate, lactate, oxalate, succinate or malate and salts with another pharmaceutically acceptable inorganic or organic acids. The hydrochloride is most preferred.

The active isocarbostyril compound used according to this invention, namely the 4-(3-tert.-butylamino-2-hydroxy)propoxy-2-methylisocarbostyril or an acid addition salt thereof, when formulated into such a pharmaceutical composition such as solid preparations of powders, granules, fine granules, tablets and capsules, can be degraded with lapse of time, with the appearance of the pharmaceutical formulation containing the active isocarbostyril compound being discolored into brown, so long as the stabilising agent to be used according to this invention is not co-existing in the composition.

Now, it was surprisingly been discovered by us the first time that the particular compounds as selected from the group consisting of magnesium silicate, magnesium oxide, hydrotalcite and sodium hydrogen carbonate are remarkably effective to prevent not only the degradation of the active isocarbostyril compound with time, but also the discoloration of the isocarbostyril-containing composition in appearance from taking place, and that said particular compounds are useful as the stabilizing agent for the active isocarbostyril compound. The stabilizing compound as above is necessary to be used in an amount of at least 0.5 parts by weight per 1.0 part by weight of the active isocarbostyril compound present, but the stabilizing compound may normally be used in an amount of ranging from 0.5 to 20 parts by weight, and preferably of ranging from 1 to 3 parts by weight per 1.0 part by weight of the active isocarbostyril compound for the stabilization purpose.

Besides, it has now been found that the stabilizing effects of the particular compounds as specified above are not or substantially not inhibited by the co-existence of conventional excipient materials which are usually incorporated in the pharmaceutical formulations or preparations and which are known as the ordinary pharmaceutically acceptable solid carriers, including anhydrous silicic acid (so-called silica), magnesium methasilicate aluminate, synthetic aluminum silicate, calcium hydrogen phosphate, lactose, powdered sugar, corn starch, microcrystalline cellulose, hydroxypropyl starch, glycine and the like.

The stabilized pharmaceutical composition according to this invention may be formulated in a known manner into various forms such as powder, granules, fine granules, tablets and hard capsules.

Accordingly, the stabilized pharmaceutical composition according to this invention comprises the active ingredient isocarbostyril compound and a stabilizing effective amount of at least one of the stabilizing compounds as specified above, and if necessary, it may further contain one or more of the solid carriers such as silica, magnesium methasilicate aluminate, synthetic aluminum silicate, dibasic calcium phosphate, lactose, powdered sugar, corn starch, microcrystalline cellulose, hydroxypropyl starch, glycine and the like; pharmaceutically acceptable binders such as gum arabic, gelatin, gum tragacanth, hydroxypropyl cellulose, polyvinyl pyrrolidone; lubricants such as magnesium stearate, talc, hardened vegetable oil; disintegrators such as carboxymethyl cellulose, calcium carboxymethyl cellulose; and wetting agents such as polyethylene glycol, sorbitol, glycerine, hydrogenated castor oil, and sodium lauryl sulfate.

The stabilized pharmaceutical composition according to this invention may be a formulation comprising as the active ingredient [4-(3-tert.-butylamino-2-hydroxy)-propoxy-2-methylisocarbostyril] or an acid addition salt thereof and at least one of the stabilizing compounds specified above, in association with at least one of pharmaceutically acceptable carriers.

The pharmaceutical composition in the form of powder may be prepared in a known manner by mixing uniformly the pulverized active ingredient compound with one or more of the powdered stabilizing agents and also with one or more of the solid carrier powders in appropriate proportions of them with aid of a conventional mixer.

The pharmaceutical composition in the form of granules or fine granules may be prepared in a known manner by mixing the active ingredient compound with one or more of the stabilizing agents and with one or more of the solid carriers in appropriate proportions above, and then adding to the resultant mixture a proper amount of a binder, followed by kneading and granulating the resulting admixture in a granulator. The binder available for this purpose may be a known pharmaceutically acceptable binder, such as a solution of hydroxypropyl cellulose in ethanol. The granulated product so obtained is dried and the dried granules are screened to separate the granules of controlled particle sizes, so that the pharmaceutical composition is prepared in the form of granules or fine granules having desired particle size(s).

The pharmaceutical composition in the form of tablets may be prepared in a known manner by mixing the granules prepared as above with an appropriate amount of lubricant and compressing the resultant mixture into tablets by means of a tableting machine.

The pharmaceutical composition in the form of hard capsules may be prepared in a known manner by mixing the granular product obtained as above with an appropriate lubricant such as magnesium stearate and talc and also with a wetting agent such as polyethylene glycol, and then filling the resultant mixture into hard gelatin capsules by means of a conventional capsule-filling machine.

According to another aspect of this invention, there is provided a method for stabilizing the isocarbostyril compound, 4-(3-tert.-butylamino-2-hydroxy)propoxy-2-methylisocarbostyril or an acid addition salt thereof, which comprises adding to and mixing with the isocarbostyril compound at least one of magnesium silicate, magnesium oxide, hydrotalcite and sodium hydrogen carbonate in an amount sufficient to stabilize the isocarbostyril compound.

This invention will be illustrated with reference to the following Examples in which some pharmaceutical formulations according to this invention are shown and to which this invention is not limited. Unless otherwise stated, all proportions of the constituents shown for the formulations are given in parts by weight.

EXAMPLE 1

Several pharmaceutical formulations each in the form of powder were prepared from the constituents indicated in Table 1 below and in the proportions (parts by weight) shown there.

TABLE 1

| Constituents | Formulation A | Formulation B | Formulation C | Formulation D |
| --- | --- | --- | --- | --- |
| 4-(3-tert.-butylamino-2-hydroxy)propoxy-2-methylisocarbostyril hydrochloride (Active ingredient) | 10.0 | 10.0 | 10.0 | 10.0 |
| Magnesium silicate | 10.0 | — | — | — |
| Magnesium oxide | — | 10.0 | — | — |
| Sodium hydrogen carbonate | — | — | 10.0 | — |
| Hydrotalcite | — | — | — | 10.0 |
| Potato starch | 240.0 | 240.0 | 240.0 | 240.0 |
| Lactose | 240.0 | 240.0 | 240.0 | 240.0 |

All the constituents indicated for each formulation were uniformly mixed together in a mixer to yield the stabilized pharmaceutical compositions in the form of powder.

EXAMPLE 2

Several pharmaceutical formulations each in the form of granules or fine granules were prepared from the constituents indicated in Table 2 below and in the proportions shown.

TABLE 2

| Constituents | Formulation E | Formulation F | Formulation G | Formulation H |
| --- | --- | --- | --- | --- |
| 4-(3-tert.-butylamino-2-hydroxy)propoxy-2-methylisocarbostyril hydrochloride | 100.0 | 100.0 | 100.0 | 100.0 |
| Magnesium silicate | 400.0 | — | — | — |
| Magnesium oxide | — | 400.0 | — | — |
| Sodium hydrogen carbonate | — | — | 400.0 | — |
| Hydrotalcite | — | — | — | 400.0 |
| Hydroxypropyl cellulose | 20.0 | 20.0 | 20.0 | 20.0 |
| Basic calcium phosphate | 380.0 | 380.0 | 380.0 | 380.0 |
| Lactose | 100.0 | 100.0 | 100.0 | 100.0 |

All the constituents indicated above for each formulation E to H, except hydroxylpropyl cellulose, were mixed together, and to the mixture obtained was added a solution of 5% hydroxylpropyl cellulose in ethyl alcohol. The resulting mixture was kneaded and then granulated into granules in an extruder-type granulator. The granulated product was dried, and then some agglomerates as formed of the dried granules were de-agglomerated and screened to separate granules of controlled particle sizes as desired. The pharmaceutical composition in the form of granules having particle sizes of 12 to 48 meshes was thus prepared each from the formulations E and F, and the pharmaceutical compositions in the form of fine granules having particle sizes of 32 to 150 meshes was prepared each from the formulations G and H.

EXAMPLE 3

The pharmaceutical compositions in the form of tablets having the following formulations were prepared from the constituents indicated in Table 3 below.

TABLE 3

| Constituents | Formulation I | Formulation J | Formulation K | Formulation L |
| --- | --- | --- | --- | --- |
| 4-(3-tert.-butylamino-2-hydroxy)propoxy-2-methylisocarbostyril hydrochloride | 20.0 | 20.0 | 20.0 | 20.0 |
| Magnesium silicate | 20.0 | — | — | — |
| Magnesium oxide | — | 20.0 | — | — |
| Sodium hydrogen carbonate | — | — | 20.0 | — |
| Hydrotalcite | — | — | — | 20.0 |
| Hydroxypropyl cellulose | 7.5 | 7.5 | 7.5 | 7.5 |
| Lactose | 98.0 | 98.0 | 98.0 | 98.0 |
| Magnesium stearate | 1.5 | 1.5 | 1.5 | 1.5 |
| Hydrogenated vegetable oil | 3.0 | 3.0 | 3.0 | 3.0 |

The active ingredient compound, i.e., 4-(3-tert.-butylamino-2-hydroxy)propoxy-2-methylisocarbostyril hydrochloride, together with magnesium silicate (or magnesium oxide, sodium hydrogen carbonate or hydrotalcite in place of the magnesium silicate) and lactose were well mixed with each other. The mixture obtained was kneaded with a solution of 5% hydroxypropyl cellulose in ethyl alcohol, followed by granulating the mixture to give granules of suitable particle sizes. These granules were dried and some agglomerates as formed of the granules were de-agglomerated into individual granules. These granules thus prepared were then admixed well with magnesium stearate and hydrogenated vegetable oil so that the granules were uniformly coated with the mixture of magnesium stearate and the oil. The granule product so obtained was compressed in a rotary tableting machine to provide tablets (each 7.0 mm in diameter, 150 mg weight and 6 kg in hardness).

EXAMPLE 4

The pharmaceutical compositions in the form of hard capsules having the following formulations were prepared from the constituents indicated in Table 4 below.

TABLE 4

| Constituents | Formulation M | Formulation N | Formulation O | Formulation P |
| --- | --- | --- | --- | --- |
| 4-(3-tert.-butylamino-2-hydroxy)propoxy-2-methylisocarbostyril hydrochloride | 50.0 | 50.0 | 50.0 | 50.0 |
| Magnesium silicate | 100.0 | — | — | — |
| Magnesium oxide | — | 100.0 | — | — |
| Sodium hydrogen carbonate | — | — | 100.0 | — |
| Hydrotalcite | — | — | — | 100.0 |
| Carboxymethyl cellulose | 7.5 | 7.5 | 7.5 | 7.5 |
| Corn starch | 85.0 | 85.0 | 85.0 | 85.0 |
| Magnesium stearate | 2.5 | 2.5 | 2.5 | 2.5 |
| Hydrogenated vegetable oil | 5.0 | 5.0 | 5.0 | 5.0 |

To prepare these formulations, corn starch was firstly mixed with a solution of 3% carboxymethyl cellulose in ethyl alcohol. The resultant mixture was kneaded and formed into granules of appropriate particle sizes which were then dried, and some agglomerates as formed of the granules were de-agglomerated into individual granules having controlled particle sizes, affording the blank granules. The blank granules were uniformly mixed with magnesium silicate (or magnesium oxide, sodium bicarbonate or hydrotalcite in place of the magnesium silicate), the active isocarbostyril compound, magnesium stearate and hydrogenated vegetable oil. The mixture so obtained was charged at a quantity of 250 mg per capsule into hard gelatin capsules of No. 3 size (products of Elanco Co.) using a hard capsule-filling machine. The pharmaceutical composition in the form of hard capsules was thus obtained.

The stabilizing effects of the particular compounds used as the stabilizing agents according to this invention are now demonstrated with reference to the following Test Example.

TEST EXAMPLE

To test the stabilizing effects of magnesium silicate, magnesium oxide, hydrotalcite and sodium hydrogen carbonate on the 4-(3-tert.-butylamino-2-hydroxy)-propoxy-2-methylisocarbostyril (hereinafter referred to merely as active ingredient), this isocarbostyril compound (the hydrochloride) alone or such formulations under test (in the powder form) each consisting of a mixture of the constituents (including the active ingredient) indicated in Tables 5, 6 and 7 below which have been prepared by mixing the constituent substances in the proportions of the constituents shown in the Tables 5-7 were stored under storage conditions of 40° C. and a relative humidity of 80%. On several days during the storage, the degree of discoloration of the sample formulations under test and the effective content of the active ingredient in the samples were evaluated.

The degree of discoloration was evaluated according to a standard method of estimating the discoloration of drugs in term of the following scales:
—: No discoloration
+: Dotted discoloration
++: Wholly discolored into yellow
+++: Wholly discolored into brown The content of the active ingredient in the sample formulations was assayed according to a high performance liquid chromatographic determination method with a reversed phase column, and the determined content of the active ingredient was calculated in percentage (by weight) based on the determined content of the active ingredient which was determined just on the day of preparing the formulations under test.

The test results obtained are summarized in Tables 5-7.

TABLE 5

| Formulations under test | Proportions of constituents mixed | Days of Storage | | | | | Content of Active ingredient (%) | |
| --- | --- | --- | --- | --- | --- | --- | --- | --- |
| | | 1 day | 3 days | 5 days | 7 days | 10 days | On 3rd day of storage | On 10th day of storage |
| Active ingredient + Magnesium silicate | 1:1 | — | — | — | — | — | 100.4 | 96.5 |
| Active ingredient + | 1:1 | — | — | — | — | — | 99.5 | 96.5 |

TABLE 5-continued

| Formulations under test | Proportions of constituents mixed | Days of Storage | | | | | Content of Active ingredient (%) | |
| --- | --- | --- | --- | --- | --- | --- | --- | --- |
| | | 1 day | 3 days | 5 days | 7 days | 10 days | On 3rd day of storage | On 10th day of storage |
| Active ingredient + Magnesium oxide | 1:1 | — | — | — | — | — | 100.2 | 96.4 |
| Active ingredient + Hydrotalcite | 1:1 | — | — | — | — | — | 96.7 | 90.5 |
| Active ingredient + Sodium hydrogen carbonate | 1:1 | — | — | — | — | + | 96.7 | 90.5 |
| Active ingredient Alone | — | — | ++ | +++ | +++ | +++ | 96.0 | 52.1 |
| Active ingredient + Microcrystalline cellulose | 1:1 | + | ++ | ++ | ++ | ++ | 8.2 | 2.6 |
| Active ingredient + Calcium hydrogen phosphate | 1:1 | + | +++ | +++ | +++ | +++ | 94.7 | 63.3 |
| Active ingredient + Corn starch | 1:1 | + | +++ | +++ | +++ | +++ | 59.2 | 51.3 |
| Active ingredient + Lactose | 1:1 | ++ | +++ | +++ | +++ | +++ | 40.5 | 25.0 |

TABLE 6

| Formulations under test | | | Proportions of constituents mixed | Days of Storage | | | | | Content of active ingredient (%) (on 10th day of storage) |
| --- | --- | --- | --- | --- | --- | --- | --- | --- | --- |
| | | | | 1 day | 3 days | 5 days | 7 days | 10 days | |
| Active ingredient | + Magnesium silicate | | 1:1 | — | — | — | — | — | 96.5 |
| Active ingredient | + Magnesium silicate | | 1:2 | — | — | — | — | — | 99.5 |
| Active ingredient | + Magnesium silicate | | 1:4 | — | — | — | — | — | 99.8 |
| Active ingredient | + Magnesium silicate | | 1:20 | — | — | — | — | — | 100.1 |
| Active ingredient | + Magnesium silicate | + Sodium hydrogen carbonate | 1:0.5:0.5 | — | — | — | — | — | 94.5 |
| Active ingredient | + Magnesium oxide | | 1:1 | — | — | — | — | — | 96.5 |
| Active ingredient | + Magnesium oxide | | 1:2 | — | — | — | — | — | 99.6 |
| Active ingredient | + Magnesium oxide | | 1:4 | — | — | — | — | — | 100.1 |
| Active ingredient | + Magnesium oxide | | 1:20 | — | — | — | — | — | 99.5 |
| Active ingredient | + Hydro talcite | | 1:1 | — | — | — | — | — | 96.4 |
| Active ingredient | + Hydro talcite | | 1:2 | — | — | — | — | — | 100.2 |
| Active ingredient | + Hydro talcite | | 1:4 | — | — | — | — | — | 99.4 |
| Active ingredient | + Hydro talcite | | 1:20 | — | — | — | — | — | 99.7 |
| Active ingredient | + Sodium hydrogen carbonate | | 1:1 | — | — | — | — | + | 90.5 |
| Active ingredient | + Sodium hydrogen carbonate | | 1:2 | — | — | — | — | + | 91.4 |
| Active ingredient | + Sodium hydrogen carbonate | | 1:4 | — | — | — | — | + | 90.6 |
| Active ingredient | + Sodium hydrogen carbonate | | 1:20 | — | — | — | — | + | 90.4 |

TABLE 7

| Formulations under test | | | Proportions of constituents mixed | Days of Storage | | | | | Content of active ingredient (%) (on 10th day of storage) |
| --- | --- | --- | --- | --- | --- | --- | --- | --- | --- |
| | | | | 1 day | 3 days | 5 days | 7 days | 10 days | |
| Active ingredient | + Magnesium silicate | + Lactose | 1:0.5:1 | — | — | — | — | — | 96.0 |
| Active ingredient | + Magnesium silicate | + Lactose | 1:1:1 | — | — | — | — | — | 96.3 |
| Active ingredient | + Magnesium silicate | + Lactose | 1:2:1 | — | — | — | — | — | 99.4 |
| Active ingredient | + Magnesium silicate | + Lactose | 1:4:1 | — | — | — | — | — | 99.5 |

TABLE 7-continued

| Formulations under test | | | Proportions of constituents mixed | Days of Storage | | | | | Content of active ingredient (%) (on 10th day of storage) |
| --- | --- | --- | --- | --- | --- | --- | --- | --- | --- |
| | | | | 1 day | 3 days | 5 days | 7 days | 10 days | |
| Active ingredient + Magnesium silicate + Micro crystalline cellulose | | | 1:0.5:1 | — | — | + | + | ++ | 76.5 |
| Active ingredient + Magnesium silicate + Micro crystalline cellulose | | | 1:1:1 | — | — | — | — | — | 95.0 |
| Active ingredient + Magnesium silicate + Micro crystalline cellulose | | | 1:2:1 | — | — | — | — | — | 99.1 |
| Active ingredient + Magnesium silicate + Micro crystalline cellulose | | | 1:4:1 | — | — | — | — | — | 99.3 |
| Active ingredient + Magnesium oxide + Lactose | | | 1:0.5:1 | — | — | — | — | — | 95.5 |
| Active ingredient + Magnesium oxide + Lactose | | | 1:1:1 | — | — | — | — | — | 96.4 |
| Active ingredient + Magnesium oxide + Lactose | | | 1:2:1 | — | — | — | — | — | 99.6 |
| Active ingredient + Magnesium oxide + Lactose | | | 1:4:1 | — | — | — | — | — | 99.5 |
| Active ingredient + Magnesium oxide + Micro crystalline cellulose | | | 1:0.5:1 | — | — | — | — | — | 96.0 |
| Active ingredient + Magnesium oxide + Micro crystalline cellulose | | | 1:1:1 | — | — | — | — | — | 96.4 |
| Active ingredient + Magnesium oxide + Micro crystalline cellulose | | | 1:2:1 | — | — | — | — | — | 99.8 |
| Active ingredient + Magnesium oxide + Micro crystalline cellulose | | | 1:4:1 | — | — | — | — | — | 99.0 |

What we claim is:

1. A stabilized pharmaceutical composition in the form of a solid preparation which comprises 4-(3-tert.-butylamino-2-hydroxy)propoxy-2-methylisocarbostyril or a pharmaceutical acceptable acid addition salt thereof as the active ingredient, and 0.5 to 20 parts by weight of one or more stabilizing agents selected from the group consisting of magnesium silicate, magnesium oxide, hydrotalcite and sodium hydrogen carbonate per one part by weight of the isocarbostyril compound.

2. A stabilized pharmaceutical composition in the form of a solid preparation which comprises 4-(3-tert.-butylamino-2-hydroxy)propoxy-2-methylisocarbostyril or a pharmaceutically acceptable acid addition salt thereof as the active ingredient, and 0.5 to 20 parts by weight of one or more stabilizing agents selected from the group consisting of magnesium silicate, magnesium oxide, hydrotalcite and sodium hydrogen carbonate per one part by weight of the isocarbostyril compound, in association with a pharmaceutically acceptable solid carrier for the active ingredient.

3. The composition as claimed in claim 1 or claim 2 in which the pharmaceutically acceptable acid addition salt of 4-(3-tert.-butylamino-2-hydroxy)propoxy-2-methylisocarbostyril is the hydrochloride.

4. A method of stabilizing 4-(3-tert.-butylamino-2-hydroxy)propoxy-2-methylisocarbostyril or a pharmaceutically acceptable acid addition salt thereof, which comprises adding to and mixing with the isocarbostyril compound one or more stabilizing agents selected from the group consisting of magnesium silicate, magnesium oxide, hydrotalcite and sodium hydrogen carbonate in an amount of 0.5 to 20 parts by weight per one part by weight of the isocarbostyril compound.

5. The composition as claimed in claim 1 or claim 2 which is in the form of a solid preparation and which comprises a pharmaceutically acceptable acid addition salt of 4-(3-tert.-butylamino-2-hydroxy)propoxy-2-methylisocarbostyril and 1 to 3 parts by weight of magnesium silicate per one part by weight of the isocarbostyril compound.

6. The composition as claimed in claim 1 or claim 2 which is in the form of a solid preparation and which comprises a pharmaceutically acceptable acid addition salt of 4-(3-tert.-butylamino-2-hydroxy)propoxy-2-methylisocarbostyril and 1–3 parts by weight of magnesium oxide per one part by weight of the isocarbostyril compound.

7. The composition as claimed in claim 1 or claim 2 which is in the form of a solid preparation and which comprises a pharmaceutically acceptable acid addition salt of 4-(3-tert.-bytylamino-2-hydroxy)propoxy-2-methylisocarbostyril and 1–3 parts by weight of hydrotalcite per one part by weight of the isocarbostyril compound.

8. The composition as claimed in claim 1 or claim 2 which is in the form of a solid preparation and which comprises a pharmaceutically acceptable acid addition salt of 4-(3-tert.-butylamino-2-hydroxy)propoxy-2-methylisocarbostyril and 1–3 parts by weight of sodium hydrogen carbonate per one part by weight of the isocarbostyril compound.

* * * * *